(12) United States Patent
Scott et al.

(10) Patent No.: US 6,585,984 B1
(45) Date of Patent: Jul. 1, 2003

(54) DUAL COMPOSITION COSMETIC PRODUCT WITH A CONCENTRATION SENSITIVE AND AN INCOMPATIBLE ACTIVE RESPECTIVELY PLACED WITHIN FIRST AND SECOND COMPOSITIONS

(75) Inventors: Ian Richard Scott, Allendale, NJ (US); Jonathan David Hague, Jakarta (ID); Dwiwahyu Haryo Suryo, Jakarta (ID); Endah Sulistyowati, Jakarta (ID); Prem Chandar, Closter, NJ (US); Ronni Lynn Weinkauf, River Edge, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 14 days.

(21) Appl. No.: 09/713,939

(22) Filed: Nov. 16, 2000

Related U.S. Application Data

(60) Provisional application No. 60/186,907, filed on Mar. 3, 2000.

(51) Int. Cl.$^7$ ................................................. A61K 6/00
(52) U.S. Cl. ........................ 424/401; 424/400; 424/43
(58) Field of Search .................... 424/400, 401, 424/43

(56) References Cited

U.S. PATENT DOCUMENTS

| | | | | |
|---|---|---|---|---|
| 4,487,757 A | * | 12/1984 | Kiozpeoplou | ................ 424/44 |
| 5,137,178 A | * | 8/1992 | Stokes et al. | ................ 222/94 |
| 5,455,035 A | * | 10/1995 | Guerrero et al. | ............ 424/401 |
| 5,883,085 A | | 3/1999 | Blank et al. | |
| 5,914,116 A | * | 6/1999 | Suares et al. | ................ 424/401 |
| 5,935,589 A | | 8/1999 | Mukherjee et al. | |
| 6,117,433 A | * | 9/2000 | Edens et al. | ................ 424/400 |
| 6,322,798 B1 | | 11/2001 | Candau et al. | |

FOREIGN PATENT DOCUMENTS

| | | |
|---|---|---|
| WO | 96/37179 | 11/1996 |
| WO | WO/98/50012 | 11/1998 |

OTHER PUBLICATIONS

Airspray/Symbio Bulletins—1999.
International Search Report.

* cited by examiner

Primary Examiner—James M. Spear
Assistant Examiner—Charesse Evans
(74) Attorney, Agent, or Firm—Milton L. Honig

(57) ABSTRACT

A cosmetic product is provided packaged in a dispenser with separate first and second storage areas. The first of the areas contains a first cosmetic composition containing a first dermal active agent, preferably selected from keratolytic skin agents. Particularly preferred are alpha- and beta-hydroxy carboxylic acids as first dermal active placed in a composition having a pH from about 1 to about 5.5. The second area contains a second cosmetic composition with a second dermal agent incompatible with the first composition. Particularly preferred second dermal agents are retinoids, vitamins, enzymes and anti-oxidants. Most preferred is retinol. The dispenser allows transfer of the first and second compositions through an exit nozzle in a respective dispensing weight ratio of from about 30:1 to about 2:1.

20 Claims, No Drawings

DUAL COMPOSITION COSMETIC PRODUCT WITH A CONCENTRATION SENSITIVE AND AN INCOMPATIBLE ACTIVE RESPECTIVELY PLACED WITHIN FIRST AND SECOND COMPOSITIONS

This application claims the benefit of U.S. Provisional Application Serial No. 60/186,907, filed Mar. 3, 2000.

BACKGROUND OF THE INVENTION

1. Field of the Invention

The invention concerns a cosmetic product with dual compositions, preferably stored in separate compartments, each composition containing a skin active with at least one of the actives being incompatible in a composition containing the other.

2. The Related Art

A soft, supple and flexible skin has a marked cosmetic appeal. As human skin ages with advancing years, the epidermis can become folded, ridged or furrowed to form wrinkles. These signal loss of youthful appearance and herald the transition to old age. Exposure to excessive doses of sunlight accelerates the transition process. Moreover, the outer layer of the epidermis known as the stratum corneum can become dry and flaky following exposure to cold weather or excessive contact with detergents or solvents.

Science has discovered a few active substances which can counter the aging process. Among these are the retinoids and the alpha-hydroxy carboxylic acids. Unfortunately these active substances can be incompatible under certain conditions. Retinol rapidly degrades in a acidic environment that may be most conducive to the alpha-hydroxys. Combinations of these actives have been reported in U.S. Pat. No. 5,935,589 (Mukhedjee et al.) which places the actives in separate emulsions within a single composition. Retinol is stabilized at a neutral pH in an oil-in-water emulsion. An alpha-hydroxy carboxylic acid such as glycolic acid is dispersed within a water-in-oil emulsion. Both of these emulsions are then carefully combined to form a single cosmetic composition. A problem for such compositions is that over time there will be leakage between the separate emulsions resulting in retinol degradation.

A more direct solution is placement of the different actives into compositions held in separate compartments of a dispenser. Illustrative is U.S. Pat. No. 5,914,116 (Suares et al.) disclosing releasably lockable stackable jars and dual compartment pumps. These packages are designed to deliver the separate actives at different times rather than through simultaneous dosing. In U.S. Pat. No. 5,137,178 (Stokes et al.) a dual compartmented squeezable cosmetic dispenser is disclosed which allows for simultaneous extrusion of separate composition streams.

While each of the aforementioned systems have their particular advantage, they introduce certain disadvantages. Actives placed in dual stream dispensing compartments must be doubly concentrated. Only half of each stream contributes to the final dispensed combined stream concentration. For instance, delivery of 8% alpha-hydroxy carboxylic acid requires a 16% concentrated stream from an equally dispensing dual stream package. High concentration presents problems. Significant skin irritation and erythema may result from localized, non-fully mixed deposition of the stream onto the skin. Internal stability at high concentration may also be compromised. There is need for a better solution.

WO 98/50012 (Noordam et al.) discusses the problem of stabilizing a low pH emulsion of Vitamin C to prevent oxidation of the active. Stabilization is achieved by placing a relatively concentrated aqueous Vitamin C composition in one compartment of a multi-compartment dispensing system. A second compartment contains a cosmetic carrier composition. When ready for use, a small volume of the Vitamin C concentrate is dispensed alongside a larger volume of the carrier base, each being expressed from a separate compartment.

A similar approach has been disclosed by Airspray® in product brochure literature for their Symbio dual-chamber dispenser. Two non-compatible ingredients are separated each from the other until the moment of application. The Symbio package has two separate chambers each connected to its own pump, one of the chambers being smaller and arranged to deliver a concentrate of an unstable cosmetic substance. Among the unstable substances mentioned are Vitamin A (retinol), Vitamin C (ascorbic acid) and Vitamin E (alpha-tocopherol). There is no suggestion that the larger container included any skin actives other than some enzymes and pigmentation control agents. The technology does not present a solution for delivering actives from a dual compartment in a manner that provides nearly identical stored and skin delivered concentrations. Focus is rather upon an active that is stored highly concentrated but delivered dilute.

Accordingly, it is an object of the present invention to provide a cosmetic product that can deliver to the skin a first dermal active agent in a concentration not substantially different from its stored concentration and simultaneously from a separate stream deliver a second dermal active incompatible with the first.

A further object of the present invention is to provide a cosmetic product that delivers an acidic first dermal active to skin at a concentration not substantially different from its stored concentration simultaneously with a second dermal active pH incompatible with the first dermal active.

Still a further object of the present invention is to provide a cosmetic product that delivers a combination of first and second dermal actives from separate compositions in a manner assuring a synergistic skin benefit effect of the combination.

Yet a further object of the present invention is to provide a cosmetic product that delivers a combination of first and second dermal actives from separate compositions in a manner which is relatively non-irritating to the skin.

These and other objects of the present invention will become more readily apparent from consideration of the following summary and detailed description.

SUMMARY OF THE INVENTION

A cosmetic product is provided which includes:
(i) a first cosmetic composition including from about 0.1 to about 20% by weight of said first composition of a first dermal active in a pharmaceutically acceptable carrier, the first dermal active being capable of irritating the skin;
(ii) a second cosmetic composition including from about 0.01 to about 20% by weight of said second composition of a second dermal active incompatible with the first cosmetic composition and delivered in a pharmaceutically acceptable carrier; and
(iii) a dispenser with first and second areas to separately store the respective first and second cosmetic compositions, and wherein the first and second compositions are dispensed to an exit nozzle in a respective dispensing weight ratio of from about 30:1 to about 2:1.

DETAILED DESCRIPTION OF THE INVENTION

Now it has been found that a first dermal active can be delivered to skin at concentrations not much different than its storage concentration and simultaneously be combined with a separately stored second dermal active incompatible with the first. Unequal volumes of the two compositions at the point of use are transferred from a dispenser. The weight ratio of first to second cosmetic composition may range from about 30:1 to about 2:1, preferably from about 15:1 to about 8:1, optimally about 11:1. By this arrangement, the first dermal active is delivered in a concentration not much than about 10 or 20% less than its stored concentration.

Delivery of the compositions of the present invention may be through a dual compartment dispenser. A particularly useful device is sold by Airspray International Inc. under the package trademark of Symbio®. The package has two separate chambers, each connected to its own pump. Both pumps are activated by the same actuator. By depressing the actuator, compositions held in each of the chambers are simultaneously pumped out and mixed in a controlled ratio. One of the chambers is a traditional container connected to its own pump by means of a dip tube. Within that chamber is a smaller one in the form of a cartridge equipped with a plug in the bottom, which moves up during use thus keeping both the cartridge and its contents air-free. Each pump stroke delivers approximately 0.4 grams of product. Per stroke the product delivery ratio between the first outer container and the cartridge is about 11:1.

Pump systems are not the only type of dispensers useful for the present invention. Delivery may be through a squeezable plastic tube containing two discrete compositions stored in separate areas one above the other in a manner similar to systems for striping toothpaste. Illustrative of this technology is U.S. Pat. No. 4,211,341 (Weyn) herein incorporated by reference.

First dermal actives may be selected from a wide range of substances, especially keratolytic agents such as alpha- and beta-hydroxycarboxylic acids. The invention is particularly useful for hydroxycarboxylic acids because of their high level of irritancy and requirements for separation from many other actives susceptible to decomposition by low pH conditions. Thus, advantageously the first composition will maintain a low pH environment ranging from about 1 to about 5.5, preferably from about 2 to about 4.5.

It has been noted that a low pH alpha-hydroxy carboxylic acid containing composition has serious skin stinging consequences if used at too high a concentration. Where a level of 10% alpha-hydroxy carboxylic acid is desired to be placed onto the skin, a dual compartment container that delivers equal volumes from each compartment must store a 20% concentration alpha-hydroxy carboxylic acid. The double strength active at that level is extremely stinging. The present invention avoids the problem by permitting delivery of the alpha-hydroxy carboxylic acid at a level much less than at double strength.

In a preferred embodiment, the first of the compositions according to the present invention contains at least one alpha-hydroxy carboxylic acid as the first dermal active agent. The alpha-hydroxy carboxylic acids are represented by formula I having the structure:

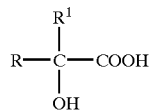

wherein R and $R^1$ are H, F, Cl, Br, alkyl, aralkyl or aryl groups of saturated or unsaturated, isomeric or nonisomeric, straight or branched chain, having 1 to 25 carbon atoms, or cyclic form having 5 or 6 ring members, and in addition, R and $R^1$ may carry OH, CHO, COOH and alkoxy groups having 1 to 9 carbon atoms, the alpha-hydroxy acid existing as a free acid, and as stereoisomers, and D, L, and DL forms when R and $R^1$ are not identical.

Illustrative of this group of materials are 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxy 2-hydroxyheptanoic acid; 2-hydroxyoctanoic acid; 2-hydroxynon anoic acid; 2-hydroxydecanoic acid; 2-hydroxyundecanoic acid; 2-hydroxydodecanoic acid (alpha-hydroxylauric acid); 2-hydroxytetradecanoic acid (alpha-hydroxymyristic acid); 2-hydroxyhexadecanoic acid (alpha-hydroxypalmitic acid); 2-hydroxyoctadecanoic acid (alpha-hydroxystearic acid); 2-hydroxyeicosanoic acid (alpha-hydroxyarachidonic acid); 2-phenyl 2-hydroxyethanoic acid (mandelic acid); 2,2-diphenyl 2-hydroxyethanoic acid (benzilic acid); 3-phenyl 2-hydroxypropanoic acid (phenyl lactic acid); 2-phenyl 2-methyl 2-hydroxyethanoic acid (atrolactic acid); 2-(4'-hydroxyphenyl) 2-hydroxyethanoic acid; 2-(4'-chlorophenyl 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3'-(2-hydroxyphenyl) 2-hydroxypropanoic acid; 3-(4'-hydroxyphenyl) 2-hydroxypropanoic acid; and 2-(3',4'-dihydroxyphenyl) 2-hydroxyethanoic acid.

Most preferred of this group of materials are glycolic acid, lactic acid and 2-hydroxyoctanoic acid (also known as hydroxycaprylic acid). Levels of alpha-hydroxy carboxylic acids may range from about 0.1 to about 20%, preferably between about 1 and 12%, more preferably between about 4 and about 10% by weight of the first composition.

When the first dermal active is a beta-hydroxy carboxylic acid, the most preferred is salicylic acid. Also suitable are $C_1$–$C_{10}$ alkyl salicylic acids such as 5-n-octanoylsalicylic acid.

Cosmetic compositions containing the hydroxy carboxylic acids preferably have a pH ranging from about 1 to about 5.5, preferably from about 2.5 to about 4.5, optimally between about 3 and about 4.

The first compositions are ordinarily aqueous emulsions of the oil-in-water or water-in-oil type. Most preferably, the first compositions are oil-in-water type emulsions. Amounts of water may range from about 20 to about 90%, preferably from about 40 to about 70%, optimally from about 50 to about 65% by weight.

By the term "pharmaceutically acceptable carrier" is meant either water, oil or a combination of water and oil phases. A variety of water soluble and water insoluble substances may constitute the respective phases.

Emollient substances are particularly useful. These may include silicone oils, synthetic esters, fatty acids, fatty alcohols, humectants (especially polyhydric alcohols) and thickeners/viscosifiers.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers (e.g. dimethicone copolyol). The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl esters of fatty acids having 10 to 20 carbon atoms. Examples thereof include methyl myristate, methyl stearate, oleyl myristate, oleyl stearate, and butyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and all-fatty acid esters, propylene glycol mono- and di-fatty acid esters, polypropylene glycol 2000 mono-oleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Also useful as emollients are $C_8$–$C_{22}$ fatty acids. These include lauric acid, myristic acid, palmitic acid, oleic acid, linoleic acid, stearic acid, behenic acid, erucic acid and mixtures thereof. Amounts of fatty acid may range from about 0.1 to about 20%, preferably from about 1 to about 15%, optimally from about 2 to about 10% by weight of either first or second compositions. Most preferred is stearic acid.

Fatty alcohols having from 8 to 22 carbon atoms may also be employed. Typical fatty alcohols include lauryl alcohol, myristyl alcohol, palmityl alcohol, oleyl alcohol, stearyl alcohol, linoleyl alcohol, behenyl alcohol and mixtures thereof. Most preferred is palmityl alcohol. Amounts of the fatty alcohol may range from about 0.05 to about 20%, preferably from about 0.1 to about 10%, optimally from about 0.2 to about 1% by weight of either first or second compositions.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, isoprene glycol, hexylene glycol, 1,3-butylene glycol, 1,2,6-hexanetriol, ethoxylated glycerol, propoxylated glycerol and mixtures thereof. The amount of humectant may range anywhere from about 0.5 to about 30%, preferably between 1 and 15% by weight of either first or second compositions.

Thickeners/viscosifiers in amounts up to about 5% by weigh of the first or second composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose) which is polyacrylamide such as found in Sepigel 305® and Scierotium gums, magnesium aluminum silicates sold as Veegum® and aluminum octenyl starches such as Dry Flo®.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium. compounds. Cosmetic chemists are familiar with appropriate preservatives and routinely choose them to satisfy the preservative challenge test and to provide product stability. Particularly preferred preservatives are disodium EDTA, butylated hydroxy toluene, phenoxyethanol, methyl paraben, butyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the first or second compositions.

Colorants and fragrances may also be included in compositions of the present invention. Each of these substances may range from about 0.05 to about 5%, preferably between about 0.1 and about 3% by weight for the first or second compositions.

Sunscreens may be included in compositions of the present invention. These may be of the organic or inorganic variety. The inorganic sunscreens include titanium dioxide, zinc oxide and mixtures thereof. Typical organic sunscreens may be classified into such groups as: para-amino benzoates, salicylates, cinnamates, benzophenones and combinations thereof. Particularly preferred are octyl methoxy cinnamate (available as Parsol MCX®), 2-hydroxy-4-methoxy benzophenone (known as Benzophenone-3) and Avobenzene (available as Parsol 1789®). Amounts of the sunscreen may range from about 0.1 to about 10%, preferably from about 5 to about 12% by weight of first or second compositions.

Surfactants may also be employed in compositions of the present invention. They may be of the cationic, anionic, nonionic or amphoteric variety. Nonionic surfactants include alkoxylated, fatty alcohols, alkoxylated fatty acids and alkoxylated sorbitan esters. They also may include alkyl polyglycosides and gluconamides. Anionic surfactants may include alkyl sulphates, alkyl ether sulphates, acyl isethionates, lactylates, sarcosinates, taurates and combinations thereof. Suitable amphoteric surfactants include cocoamidopropyl betaine and dimethyl alkyl amine oxides. Amounts of the surfactant may range anywhere from about 0.1 to about 10%, preferably from about 1 to about 5% by weight of first or second compositions.

The second composition of this invention will contain a second dermal active incompatible with the first composition. By the term "incompatible" is meant that any skin benefit normally imparted by contact with the second dermal active is at least partially impaired or inactivated. Illustrative but non-limiting examples of such actives include retinoids, vitamins, enzymes and anti-oxidants as well as combinations thereof. The term "retinoids" is meant to include, retinol in all its isomeric forms including cis and trans isomers, $C_2$–$C_{22}$ retinyl esters such as retinyl acetate, retinyl propionate, retinyl linoleate, retinyl ascorbate, retinyl phosphate, retinal and its isomers, and retinoic acid as well as any combinations thereof. Vitamins suitable for the present invention are Vitamin C (including derivatives such as magnesium ascorbyl phosphate), vitamin D, niacinamide, Vitamin E and combinations thereof. Enzymes suitable for the present invention include proteases (such as triposin, alpha-chymotrypsin, papain, bromelain and pepsin), lipases, oxidases (such as glutathine peroxidase and coenzyme Q10), elastases, superoxide dismutase and combinations thereof. Anti-oxidants suitable for the present invention include green tea, hawthorn, ginkgo biloba, catechin, beta-carotene, lipoic acid, glutathione, methionine, silymarin, grapeskin/seed extracts, melanin, rosemary extracts, tocopherol sorbate and combinations thereof.

Amounts of the second dermal active may range from about 0.01 to about 20%, preferably from about 0.1 to about 10%, more preferably from about 0.8 to about 4%, optimally from about 2 to about 2.6% by weight of the second composition.

The second composition may be anhydrous or aqueous. When aqueous it may have a pH ranging from about 6.5 to about 8.5, preferably from about 7 to about 8.

The second composition may contain many of the same pharmaceutically acceptable carriers as those described above. Preferably, this composition will be of the oil-in-water type. However, ordinarily the composition will have different physical and chemical components than that of the first composition.

Except in the operating and comparative examples, or where otherwise explicitly indicated, all numbers in this description indicating amounts of material are to be understood as modified by the word "about".

The following examples will more fully illustrate the embodiments of this invention. All parts, percentages and proportions referred to herein and in the appended claims are by weight unless otherwise illustrated.

EXAMPLES 1–8

A set of first and second compositions according to the present invention are outlined in Table I below. Each of these combinations are delivered from a dual compartment package, particularly a Symbio® dual dispensing pump container.

TABLE I

| INGRE-DIENTS | EXAMPLES | | | | | | | |
|---|---|---|---|---|---|---|---|---|
| | 1 | 2 | 3 | 4 | 5 | 6 | 7 | 8 |
| Composition 1 | | | | | | | | |
| Glycolic Acid | 10.00 | 10.00 | 12.00 | 12.00 | 8.00 | 8.00 | 6.00 | — |
| Ammonia (25% Active) | 3.20 | — | 3.60 | 3.60 | 3.00 | 3.20 | 2.80 | — |
| Salicylic Acid | — | 10.00 | — | — | — | — | — | 6.00 |
| Dry Flo ® | 2.00 | 2.50 | 2.00 | 2.00 | 2.00 | 1.50 | 2.00 | 2.00 |
| Stearic Acid | 2.00 | 1.50 | 1.50 | 2.00 | 1.50 | 1.50 | 2.00 | 1.50 |
| Butylene Glycol | 2.00 | 1.50 | 1.50 | 2.00 | 1.50 | 1.50 | 2.00 | 1.50 |
| Cetiol OE ® | 2.00 | 1.50 | 2.00 | 2.00 | 2.00 | 2.00 | 2.00 | 2.00 |
| Parsol MCX ® | 2.00 | 2.00 | 2.00 | 2.00 | 2.00 | 2.00 | 2.00 | 2.00 |
| Glycerol Monostearate | 1.00 | 1.00 | 1.00 | 1.20 | 1.00 | 1.00 | 1.00 | 1.00 |
| Propylene Glycol | 1.00 | 1.00 | 1.00 | 1.00 | 1.00 | 1.00 | 1.00 | 1.00 |
| Isoprene Glycol | 1.00 | 1.00 | 1.00 | 1.00 | 1.00 | 1.00 | 1.00 | 1.00 |
| Myrj 59 ® | 1.00 | 1.00 | 1.00 | 1.00 | 1.00 | 1.00 | 1.00 | 1.00 |
| Glycerin | 1.00 | 1.00 | 1.00 | 1.00 | 1.00 | 1.00 | 1.00 | 1.00 |
| Triethanolamine | 0.80 | 0.80 | 0.80 | 0.80 | 0.80 | 0.80 | 0.80 | 0.80 |
| Sodium Bisulphite | 0.64 | 0.32 | 0.32 | 0.32 | 0.32 | 0.32 | 0.32 | 0.32 |
| Tiona AG ® | 0.50 | 0.50 | 0.50 | 0.50 | 0.50 | 0.50 | 0.50 | 0.50 |
| Veegum Ultra ® | 0.50 | 0.50 | 0.50 | 0.50 | 0.50 | 0.50 | 0.50 | 0.50 |
| Silicone Fluid | 0.50 | 0.50 | 0.50 | 0.50 | 0.50 | 0.50 | 0.50 | 0.50 |
| Finsolve ® | 0.50 | 0.50 | 0.50 | 0.50 | 0.50 | 0.50 | 0.50 | 0.50 |
| Sepigel 305 ® | 0.50 | 0.50 | 0.50 | 0.50 | 0.50 | 0.50 | 0.50 | 0.50 |
| Parsol 1789 ® | 0.40 | 0.40 | 0.40 | 0.40 | 0.40 | 0.40 | 0.40 | 0.40 |
| Cholesterol ® | 0.25 | 0.25 | 0.25 | 0.25 | 0.25 | 0.25 | 0.25 | 0.25 |
| Lorol C16 ® | 0.25 | 0.25 | 0.25 | 0.25 | 0.25 | 0.25 | 0.25 | 0.25 |
| Fragrance | 0.25 | 0.25 | 0.25 | 0.25 | 0.25 | 0.25 | 0.25 | 0.25 |
| Crodafos CES ® | 0.24 | 0.24 | 0.24 | 0.24 | 0.24 | 0.24 | 0.24 | 0.24 |
| Rhodopol 23 U ® | 0.13 | 0.13 | 0.13 | 0.13 | 0.13 | 0.13 | 0.13 | 0.13 |
| Nipasol | 0.10 | 0.10 | 0.10 | 0.10 | 0.10 | 0.10 | 0.10 | 0.10 |
| Vitamin E Acetate | 0.10 | 0.10 | 0.10 | 0.10 | 0.10 | 0.10 | 0.10 | 0.10 |
| Bisabolol | 0.10 | 0.10 | 0.10 | 0.10 | 0.10 | 0.10 | 0.10 | 0.10 |
| Natrosol 250 ® | 0.10 | 0.10 | 0.10 | 0.10 | 0.10 | 0.10 | 0.10 | 0.10 |
| Nervanaid BA 2 ® | 0.05 | 0.05 | 0.05 | 0.05 | 0.05 | 0.05 | 0.05 | 0.05 |
| Retinol | 0.02 | 0.02 | 0.02 | 0.02 | 0.02 | 0.02 | 0.02 | 0.02 |
| Hydroxycaprylic Acid | 0.01 | 0.01 | 0.01 | 0.01 | 0.01 | 0.01 | 0.01 | 0.01 |
| Vitamin A Palimitate | 0.01 | 0.01 | 0.01 | 0.01 | 0.01 | 0.01 | 0.01 | 0.01 |
| Pationic SSL ® | 0.01 | 0.01 | 0.01 | 0.01 | 0.01 | 0.01 | 0.01 | 0.01 |
| Water | Bal. | Bal. | Bal. | Bal. | Bal. | Bal. | Bal. | Bal. |
| Composition 2 | | | | | | | | |
| Cetiol OE ® | 11.88 | 10.08 | 9.88 | 9.88 | 99.88 | 6.88 | 6.88 | 13.08 |
| Tween 20 ® | 3.20 | 3.20 | 3.20 | 3.20 | 3.20 | 3.20 | 3.20 | 3.20 |
| Retinol | 2.40 | 1.80 | 2.40 | 3.00 | 1.80 | 1.50 | 2.40 | 3.50 |
| Potassium Hydroxide | 1.30 | 1.30 | 1.30 | 1.30 | 1.30 | 1.30 | 1.30 | 1.30 |
| Triethanolamine | 1.20 | 1.20 | 1.20 | 1.20 | 1.20 | 1.20 | 1.20 | 1.20 |
| Sodium Bisulphite (39% Active) | 0.52 | 0.52 | 0.52 | 0.52 | 0.52 | 0.52 | 0.52 | 0.52 |
| Carbopol Ultrez 10 ® | 0.50 | 0.50 | 0.50 | 0.50 | 0.50 | 0.50 | 0.50 | 0.50 |
| Xanthan Gum | 0.50 | 0.50 | 0.50 | 0.50 | 0.50 | 0.50 | 0.50 | 0.50 |
| Dequest 2006 ® | 0.49 | 0.40 | 0.40 | 0.80 | 0.49 | 0.49 | 0.49 | 0.49 |
| BHT | 0.20 | 0.20 | 0.20 | 0.20 | 0.20 | 0.10 | 0.20 | 0.10 |
| Glydant Plus ® | 0.20 | 0.20 | 0.20 | 0.20 | 0.20 | 0.20 | 0.20 | 0.20 |
| EDTA | 0.10 | 0.10 | 0.05 | 0.10 | 0.05 | 0.10 | 0.10 | 0.10 |

EXAMPLE 9

A clinical study was conducted to evaluate the sting reduction benefits associated with dispensing dermal actives in unequal concentration from a dual dispensing package.

Formulations

Product A 8.7% glycolic acid formula was placed in the outer chamber of the inventive example dispensing pump (Airspray). The inner chamber contained a base formula without any glycolic acid. The dispensing ratio of this package is such that when dispensed, 11 parts of the outer formula was dispensed with 1 part of the inner formula. Thus the final concentration of glycolic acid exposed to the skin in the co-dispensed product was 8%.

Product B (Comparative)

16% glycolic acid was formulated in the same base formula as in Product A and placed in one compartment of a commercially available 1:1 dispensing ratio dual chambered pump. The other chamber contained the same formula as that in the inner chamber of Product A. Thus the final concentration of glycolic acid exposed to the skin was also 8% when co-dispensed.

Test Design:

Six subjects were pre-selected on the basis of their ability to sense a, stinging or burning sensation from alpha hydroxy acid products and in addition on their ability to discriminate between formulations containing 16% glycolic acid and 8% glycolic acid. The areas of skin near each nostril and above the lip were first tapestripped with a D-squame strip to remove dirt and oil. About 3 mg of each of product A and B were dispensed on the left and right index finger of each subject. The subjects, who were blinded with respect to any knowledge about the products, were asked to apply each product on either tapestripped area at the same time. They were asked to evaluate within a minute of application as to whether they sensed a greater burning or stinging on one side compared to the other.

Results

| | |
|---|---|
| Subject 1 | B > A |
| Subject 2 | B > A |
| Subject 3 | B > A |
| Subject 4 | B = A |
| Subject 5 | B > A |
| Subject 6 | B > A |

Five out of the six subjects immediately sensed greater stinging from the product B. The results thus demonstrate that the delivery of glycolic acid in unequal dispensing ratio as set forth in this invention offers a benefit in reducing the immediate negative sensations of stinging caused by the sudden exposure of the skin to a high concentration of glycolic acid as would be encountered in the 1:1 dispensing packages.

The foregoing description and examples illustrate selected embodiments of the present invention. In light thereof variations and modifications will be suggested to one skilled in the art, all of which are within the spirit and purview of this invention.

What is claimed is:

1. A cosmetic product comprising:
   (i) a first cosmetic composition including from about 0.1 to about 20% by weight of said first composition of a first dermal active which is an alpha- or beta-hydroxy carboxylic acid in a pharmaceutically acceptable carrier, the first dermal active being capable of irritating the skin;
   (ii) a second cosmetic composition including from about 0.01 to about 20% by weight of said second composition of a second dermal active incompatible with the first cosmetic composition and delivered in a pharmaceutically acceptable carrier, incompatibility of the dermal actives being reflected by the second dermal active having a skin benefit which is at least partially impaired or inactivated by contact with the first dermal active; and
   (iii) a dispenser with first and second areas to separately store the respective first and second cosmetic compositions, and wherein the first and second compositions are dispensed to an exit nozzle in a respective dispensing weight ratio of from about 30:1 to about 2:1.

2. The product according to claim 1 wherein the dispensing weight ratio of first to second composition is from about 15:1 to about 8:1.

3. The product according to claim 1 wherein the second dermal active is selected from the group consisting of retinoids, vitamins, enzymes, anti-oxidants and combinations thereof.

4. The product according to claim 3 wherein the second dermal agent is retinol.

5. The product according to claim 4 wherein the retinol is present in an amount from about 0.8 to about 4% by weight of the second composition.

6. The product according to claim 1 wherein the dispenser has first and second compartments and is fitted with a pump mechanism, the pump mechanism comprising a separate pump for each of the first and second compartments.

7. The product according to claim 1 wherein the first cosmetic composition has a pH ranging from about 1 to about 5.5.

8. The product according to claim 1 wherein the second composition is anhydrous.

9. The product according to claim 1 wherein the dispenser is a flexible waited tube wherein dispensing occurs by external hand pressure against walls of the tube.

10. A cosmetic product comprising:
   (i) a first cosmetic composition including from about 0.1 to about 20% by weight of said first composition of a first dermal active which is an alpha- or beta-hydroxy carboxylic acid in a pharmaceutically acceptable carrier, the first dermal active being capable of irritating the skin;
   (ii) a second cosmetic composition including from about 0.01 to about 20% by weight of said second composition of a second dermal active which is retinol incompatible with the first cosmetic composition and delivered in a pharmaceutically acceptable carrier; and
   (iii) a dispenser with first and second areas to separately store the respective first and second cosmetic compositions, and wherein the first and second compositions are dispensed to an exit nozzle in a respective dispensing weight ratio of from about 30:1 to about 2:1.

11. A cosmetic product comprising:
   (i) a first cosmetic composition including from about 0.1 to about 20% by weight of said first composition of a first dermal active which is an alpha- or beta-hydroxy carboxylic acid in a pharmaceutically acceptable carrier, the first dermal active being capable of irritating the skin;
   (ii) a second cosmetic composition including from about 0.01 to about 20% by weight of said second composition of a second dermal active incompatible with the first cosmetic composition and delivered in a pharmaceutically acceptable carrier, and (iii) a dispenser with first and second areas to separately store the a respective first and second cosmetic compositions, and wherein the first and second compositions are dispensed to an exit nozzle in a respective dispensing weight ratio of from about 30:1 to about 2:1.

12. The product according to claim 11 wherein the dispensing weight ratio of first to second composition is from about 15:1 to about 8:1.

13. The product according to claim 11 wherein the first dermal active is an alpha- or beta-hydroxycarboxylic acid.

14. The product according to claim 11 wherein the second dermal active is selected from the group consisting of retinoids, vitamins, enzymes, anti-oxidants and combinations thereof.

15. The product according to claim 14 wherein the second dermal agent is retinot.

16. The product according to claim 15 wherein the retinol is present in an amount from about 0.8 to about 4% by weight of the second composition.

17. The product according to claim 11 wherein the dispenser has first and second compartments and is fitted with a pump mechanism, the pump mechanism comprising a separate pump for each of the first and second compartments.

18. The product according to claim 11 wherein the first cosmetic composition has a pH ranging from about 1 to about 5.5.

19. The product according to claim 11 wherein the second composition is anhydrous.

20. The product according to claim 11 wherein the dispenser is a flexible walled tube wherein dispensing occurs by external hand pressure against walls of the tube.

* * * * *